United States Patent [19]

Hensman et al.

[11] Patent Number: 4,792,636
[45] Date of Patent: Dec. 20, 1988

[54] PROCESS OF RECOVERING ALDEHYDES

[75] Inventors: John R. Hensman, Letchworth; Andrew J. Roberts, Milton Keynes; George E. Harrison, Billericay, all of England

[73] Assignee: Davy McKee (London) Limited, London, England

[21] Appl. No.: 68,172

[22] Filed: Jun. 30, 1987

[30] Foreign Application Priority Data

Jul. 1, 1986 [GB] United Kingdom ............... 8616037

[51] Int. Cl.$^4$ .............................................. C07C 45/78
[52] U.S. Cl. .................................. 568/492; 568/451; 568/454
[58] Field of Search ................. 568/454, 492, 451

[56] References Cited

U.S. PATENT DOCUMENTS

| | | | |
|---|---|---|---|
| 4,148,830 | 4/1979 | Pruett et al. | 568/454 |
| 4,151,209 | 4/1979 | Paul et al. | 568/454 |
| 4,247,486 | 1/1981 | Brewster et al. | 568/454 |
| 4,287,370 | 9/1981 | Harris et al. | 568/454 |
| 4,297,239 | 10/1981 | Bryant et al. | 568/454 |
| 4,322,564 | 3/1982 | Tsunoda et al. | 568/454 |
| 4,479,012 | 10/1984 | Fischer et al. | 568/454 |
| 4,577,043 | 3/1986 | Kalbfell et al. | 568/454 |

FOREIGN PATENT DOCUMENTS

| | | | |
|---|---|---|---|
| 0096986 | 12/1983 | European Pat. Off. | 45/50 |
| 0096988 | 12/1983 | European Pat. Off. | 45/50 |
| 0114611 | 1/1984 | European Pat. Off. | 45/50 |

*Primary Examiner*—Werren B. Lone
*Attorney, Agent, or Firm*—Bernard Rothwell & Brown

[57] ABSTRACT

A process is provided for the recovery of an optionally substituted $C_7$ to $C_{17}$ aldehyde from a liquid hydroformylation product medium obtained by rhodium catalyzed hydroformylation of an optionally substituted $C_6$ to $C_{16}$ olefin which contains (i) a rhodium complex hydroformylation catalyst containing rhodium in complex combination with carbon monoxide and with a ligand, (ii) excess ligand, (iii) at least one optionally substituted $C_7$ to $C_{17}$ aldehyde, and (iv) aldehyde condensation products, which process comprises:

(a) degassing said liquid hydroformylation medium;

(b) passing the degassed liquid hydroformylation medium through an evaporation zone maintained under temperature and pressure conditions conducive to evaporation of said at least one $C_7$ to $C_{17}$ aldehyde;

(c) recovering from the evaporation zone a liquid catalyst-containing stream;

(d) cooling the catalyst-containing stream exiting the evaporation zone;

(e) recovering a vaporous stream from the evaporation zone containing (i) at least one optionally substituted $C_7$ to $C_{17}$ aldehyde, (ii) ligand and (iii) a minor amount of said aldehyde condensation products;

(f) passing said vaporous stream to a fractionation zone;

(g) recovering from said fractionation zone (i) a vaporous product stream containing said at least one $C_7$ to $C_{17}$ aldehyde, and (ii) a liquid bottom stream containing said ligand and aldehyde condensation products; and (h) recycling said cooled catalyst-containing stream of step (d) and at least a part of the material of said liquid bottom stream of step (g) to said hydroformylation zone.

14 Claims, 1 Drawing Sheet

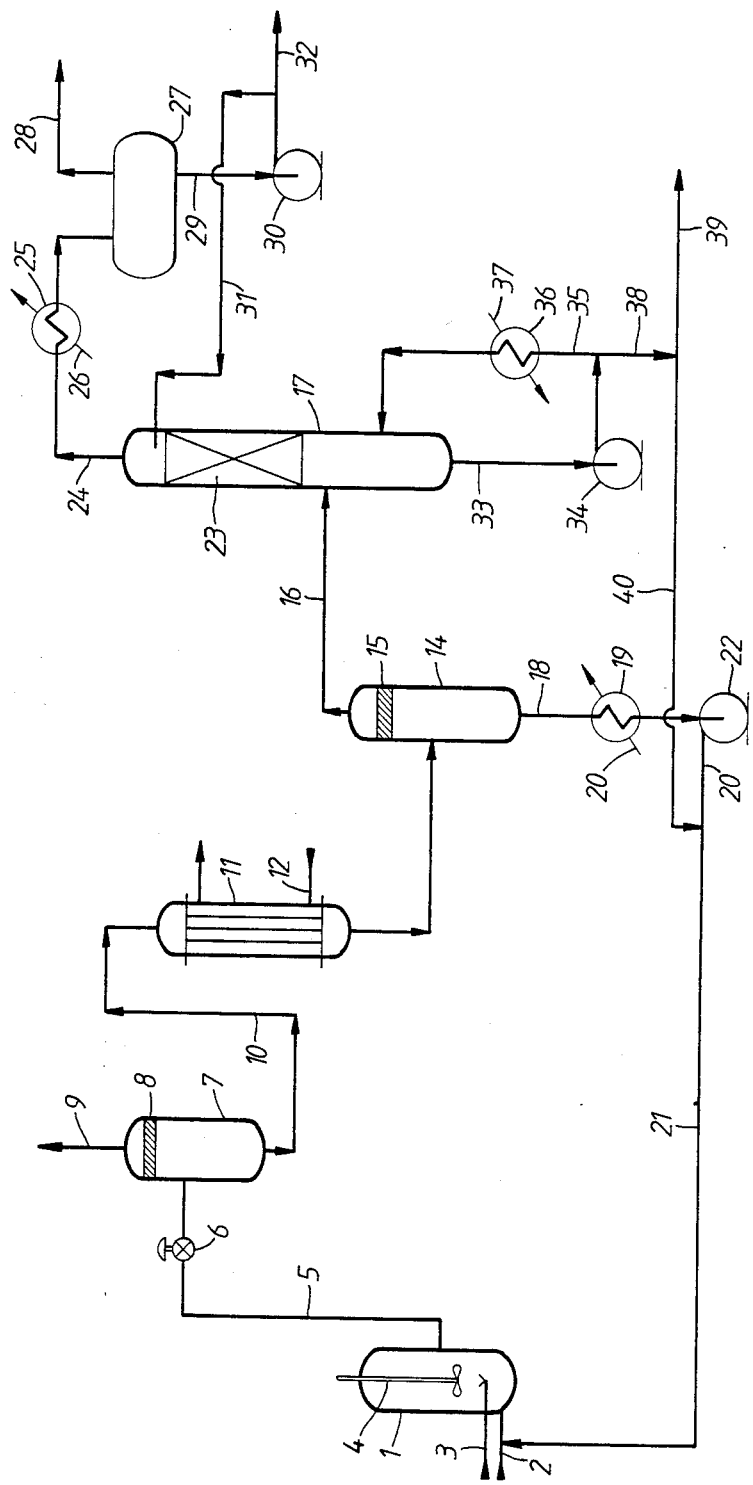

PROCESS OF RECOVERING ALDEHYDES

This invention relates to the production of aldehydes by hydroformylation of olefinic compounds. In particular it relates to the recovery of product aldehydes from the liquid hydroformylation medium.

Processes for forming aldehydes by hydroformylation of an olefin with carbon monoxide and hydrogen in the presence of a rhodium complex catalyst and free ligand, for example free triphenylphosphine ligand, are well known in the art. Thus U.S. Pat. No. 3,527,809 discloses a hydroformylation process in which olefins are hydroformylated with carbon monoxide and hydrogen in the presence of a rhodium complex catalyst and free triarylphosphine to produce aldehydes in high yields at low temperatures and pressures, the n- to iso-aldehyde isomerisation ratio of product aldehydes being high when propylene and higher olefins are used as starting olefin. It is also known that, under hydroformylation conditions, some of the product aldehydes may condense to form, as by-products, high boiling aldehyde condensation products such as aldehyde dimers or trimers. The use of these high boiling liquid aldehyde condensation products as a reaction solvent for the catalyst has been disclosed in U.S. Pat. No. 4,148,830. The nature of the aldehyde condensation products is discussed in considerable detail in U.S. Pat. No. 4,148,830 and the attention of the reader is directed to this specification for further teaching regarding the nature of such condensation products.

According to U.S. Pat. No. 4,148,830: 'Aldehydic products can be recovered from the hydroformylation reaction product mixture, for example, by first cooling the effluent from the hydroformylation zone, then passing same through a let-down valve in which the pressure is substantially reduced, e.g. atmospheric pressure. Thereafter, the effluent can be passed through a first long-tube vaporizer to flash off hydrogen, carbon monoxide, unreacted alpha-olefinic reactant, etc., at ambient temperature, and then introduced into a second long-tube, which can be maintained at elevated temperatures, e.g., about 100° or less to about 160° C. and higher, at about 1 mm of Hg to 760 mm of Hg (the operative conditions primarily depending upon the nature of the aldehydic products) to thus strip or recover the aldehydes as an overhead fraction. The liquid residue fraction comprises some unrecovered aldehydic product, free triorganophosphorus ligand, some high boiling condensation products, and hyodium values" (column 10, lines 34 to 52).

Illustrative alpha-olefinic compounds which can be employed in this process as reactants include alpha-olefins of 2 to 20 carbon atoms, preferably 2 to 10 carbon atoms.

When using $C_2$ to $C_5$ olefins the aldehyde product can be recovered from the hydroformylation reactor in the vapour state by using a gas recycle system, the rate of gas recycle being selected to vaporise aldehyde condensation products from the liquid hydroformylation reactor at the same rate as that at which they are being formed. Such a process is taught in U.S. Pat. No. 4,247,486.

U.S. Pat. No. 4,151,209 suggests continuously stripping a liquid hydroformylation medium containing a rhodium complex catalyst by gas stripping, distillation, or evaporation during the course of the hydroformylation reaction to such a degree that the ratio of (a) phosphorus contained in the liquid reaction medium in the form of high boiling organophosphorus reaction by-products (excluding alkyl-substituted derivatives of the ligand formed by substitution of the olefin into the ligand molecule and also excluding oxides of the ligand and of the alkyl-substituted derivatives) to (b) phosphorus contained in the reaction medium in the form of the ligand is maintained at a value not greater than about 0.2.

A process for the production of n-valeraldehyde by hydroformylation of butene-1 is described in U.S. Pat. 4,287,370. In this process reaction medium is passed through a let-down valve and is then heated before entering a flash drum from which is recovered a vaporous stream containing unreacted butenes and product $C_5$ aldehydes, this vaporous stream being subsequently subjected to distillation to separate the $C_5$ aldehyde products from the $C_4$ hydrocarbons.

Stripping of a partially deactivated rhodium complex catalyst containing hydroformylation reaction medium by distillation at temperatures of about 20° C. to about 350° C. under pressures of about 1000 mm Hg to about $1 \times 10^{-6}$ mm Hg to yield a rhodium complex concentrate distillation residue containing a major amount of the rhodium of the catalyst and which has been concentrated to about 0.1 to about 30% by weight of the spent hydroformylation reaction medium is disclosed in U.S. Pat. No. 4,297,239.

Whilst the prior art processes are generally satisfactory for recovery of relatively low boiling aldehydes, such as those obtained by hydroformylation of $C_2$ to $C_5$ olefins, the reduced volatility of the aldehyde products and of the aldehyde condensation by-products obtained upon hydroformylation of $C_6$ and higher olefins increases the difficulty of product recovery in a continuously operating hydroformylation process. Thus, although the use of increased temperatures in the product recovery steps can compensate for lower volatility of the product aldehydes, when hydroformylating $C_6$ and higher olefins, yet the use of higher temperatures in the product recovery zone is disadvantageous since the use of higher temperatures not only increases the rate of aldehyde by-product formation but also increases the risk of catalyst deactivation or poisoning, particularly if product recovery is effected at high temperature in the presence of CO, either of which eventualities may lead to premature shut down of the reactor due to catalyst deactivation.

EP-A-No. 0114611 discloses a process in which $C_5$ to $C_{12}$ alk-1-enes are hydroformylated in a reactor from which reaction medium is removed and passed through a heat exchanger prior to passage through a pressure reduction valve and is then passed to a degassing column. Aldehyde product is removed in the vapour phase from the degassing column, is condensed by means of a condenser and is recovered in a liquid phase from a separator, the gas phase being recirculated to the hydroformylation reactor. Aldehyde depleted reaction medium is recovered from the bottom of the degassing column, is cooled in a further heat exchanger and is recycled to the hydroformylation reactor. Provision is made for taking purge streams of the circulating gas and of the catalyst recycle solution by means of appropriate valves. This process, however, suffers from the disadvantages named above, namely the need to expose the reaction medium exiting the hydroformylation reactor to high temperatures for a relatively long time in order to effect product recovery.

The present invention seeks to provide an improved hydroformylation procedure for the production of $C_7$ and higher aldehydes by hydroformylation of $C_6$ and higher olefins in which exposure of the catalyst-containing medium to catalyst deactivating conditions is substantially obviated. It further seeks to provide a hydroformylation process in which recovery of product aldehydes is effected at a maximum temperature which is as close as possible to that prevailing in the hydroformylation zone.

According to the present invention there is provided a process for the recovery of an optionally substituted $C_7$ to $C_{17}$ aldehyde from a liquid hydroformylation product medium obtained by rhodium catalysed hydroformylation of an optionally substituted $C_6$ to $C_{16}$ olefin which contains (i) a rhodium complex hydroformylation catalyst containing rhodium in complex combination with carbon monoxide and with a ligand, (ii) free ligand, (iii) at least one optionally substituted $C_7$ to $C_{17}$ aldehyde, and (iv) aldehyde condensation products, which process comprises:

(a) degassing said liquid hydroformylation medium;

(b) passing the degassed liquid hydroformylation medium through an evaporation zone maintained under temperature and pressure conditions conducive to evaporation of said at least one $C_7$ to $C_{17}$ aldehyde;

(c) recovering from the evaporation zone a liquid catalyst-containing stream;

(d) cooling the catalyst-containing stream exiting the evaporation zone;

(e) recovering a vaporous stream from the evaporation zone containing (i) at least one optionally substituted $C_7$ to $C_{17}$ aldehyde, (ii) ligand and (iii) a minor amount of said aldehyde condensation products;

(f) passing said vaporous stream to a fractionation zone;

(g) recovering from said fractionation zone (i) a vaporous product stream containing said at least one $C_7$ to $C_{17}$ aldehyde, and (ii) a liquid bottom stream containing said ligand and aldehyde condensation products; and (h) recycling said cooled catalyst-containing stream of step (d) and at least a part of the material of said liquid bottom stream of step (g) to said hydroformylation zone.

By degassing the hydroformylation medium this is substantially freed from dissolved $H_2$ and CO, as well as from any inert gases such as $N_2$, Ar and $CH_4$ supplied to the hydroformylation zone in the synthesis gas required for the hydroformylation reaction. Removal of CO at this stage has the advantage that, in the subsequent evaporation step, heating of the catalyst-containing stream occurs substantially in the absence of CO, this reducing significantly the risk of catalyst deactivation.

Conveniently degassing is accomplished by passing the liquid hydroformylation medium from the reactor through a pressure let-down valve, so as to reduce the pressure from the elevated pressure in the hydroformylation zone to atmospheric or sub-atmospheric pressure, and then through a flash vessel from which the gases are removed, leaving the liquid phase to pass on for further treatment.

The temperature in the evaporation zone is maintained at a sufficiently high temperature to volatilise the product at the pressure prevailing therein. Typically the evaporation zone is operated at a temperature of from about 100° C. to about 170° C., more usually in the range of from about 120° C. to about 150° C. Preferably the temperature in the evaporation zone is no higher than about 150° C. and is even more preferably about 140° C. or lower.

The evaporation zone is maintained under a subatmospheric pressure. Typically the pressure in the evaporation zone ranges from about 0.0001 bar or less up to about 0.05 bar.

The residence time in the evaporation zone is preferably from about 0.5 seconds to about 5 seconds.

The evaporation zone preferably comprises a falling film evaporator or a wiped film evaporator followed by a vapour-liquid separator.

Catalyst-containing solution exiting the vapour-liquid separator is rapidly cooled before recycle to the hydroformylation zone. Conveniently the catalyst-containing solution is cooled to a temperature corresponding substantially to that prevailing in the hydroformylation zone. Cooling is preferably accomplished as soon as practicable following exit from the vapour-liquid separator.

The vaporous stream recovered from the evaporation zone in step (d) of the process of the invention is led to a fractionation zone; this can comprise a single fractionation column. In this way the pressure drop across the fractionation zone is minimised. The fractionation zone is preferably also operated at subatmospheric pressure, for example at a pressure corresponding to or less than that prevailing in the evaporation zone.

A vaporous product stream containing the product aldehyde or aldehydes, as well as unreacted olefin and a minor amount of olefin hydrogenation by-product, is recovered from the fractionation zone. Part of this vapour stream can be condensed and recycled as a reflux stream to the fractionation zone. A liquid bottom stream is also recovered from the fractionation zone which contains a minor amount of product aldehyde or aldehydes, besides ligand and aldehyde condensation products. This bottom stream usually comprises no more than about 4% of the mass flow of the vaporous product stream. At least a part of this bottom stream can be recycled to the hydroformylation zone. Alternatively the bottom stream recovered from the fractionation zone can be passed to a ligand recovery zone in which ligand is separated from aldehyde condensation products, for example by fractional distillation, and the resulting separated ligand can be recycled to the hydroformylation zone. It is also possible to recycle some of the bottom product stream from the fractionation zone to the hydroformylation zone and to treat the remainder in a ligand recovery zone, from which recovered ligand is recycled.

In another aspect, the invention relates to a process for the production of an optionally substituted $C_7$ to $C_{17}$ aldehyde by rhodium catalysed hydroformylation of an optionally substituted $C_6$ to $C_{16}$ olefin which comprises feeding said olefin and make-up quantities of carbon monoxide and hydrogen to a hydroformylation zone containing a predetermined volume of a liquid hydroformylation medium containing a rhodium complex hydroformylation catalyst comprising rhodium in complex combination with carbon monoxide and with a ligand, and excess ligand; withdrawing liquid hydroformylation medium from the hydroformylation zone; degassing this withdrawn hydroformylation medium; passing degassed liquid hydroformylation medium through an evaporation zone maintained under temperature and pressure conditions conducive to evaporation of said at least one optionally substituted $C_7$ to $C_{17}$ aldehyde; recovering from the evaporation zone a liquid catalyst-containing stream; cooling said catalyst-containing stream exiting the evaporation zone; recycling cooled catalyst-containing stream to the hydroformylation zone; recovering a vaporous stream from the evaporation zone containing said at least one optionally substituted $C_7$ to $C_{17}$ aldehyde, ligand and a minor amount of aldehyde condensation products; passing said vaporous stream to a fractionation zone; recovering from said fractionation zone a vaporous product stream containing said at least one optionally substituted $C_7$ to $C_{17}$ aldehyde and a liquid bottom stream containing ligand and aldehyde condensation products; and recycling sufficient of the material of said liquid bottom stream to said hydroformylation zone to maintain said predetermined volume of hydroformylation medium therein.

The hydroformylation conditions maintained in the hydroformylation zone are selected in dependence upon the olefin used as feedstock and upon the ligand. Generally speaking the hydroformylation conditions include use of a pressure in the range of from about 1 bar to about 100 bar and a temperature in the range of from about 40° C. to about 160° C. For details of typical hydroformylation conditions reference should be made to U.S. Pat. No. 3,527,809, U.S. Pat. No. 4,148,830, U.S. Pat. No. 4247486, EP-A-No. 0096986, EP-A-No. 0096987, EP-A-No. 0096988 and other patent specifications describing rhodium catalysed hydroformylation conditions.

The process of the invention is applicable to hydroformylation of alpha-olefinic compounds. Such compounds may contain, in addition to an alpha-olefin group of the formula $-CH:CH_2$ or $>C:CH_2$, one or more substituents which do not interfere with the hydroformylation reaction, for example one or more ether or ester groups. Illustrative alpha-olefinic compounds which can be used in the hydroformylation process of the present invention include 1-hexene, 1-heptene, 1-octene, 1-nonene, 1-decene, 1-undecene, 1-dodecene, 1-tridecene, 1-tetradecene, 1-hexadecene, 2-methyl-1-hexene, 2-methyl-1-heptene, 2-methyl-1-heptene, allyl t-butyl ether, allylpropionate and the like.

In the hydroformylation of an olefin containing an alpha-olefinic group, such as 1-decene, the ligand is preferably a triarylphosphine, such as triphenylphosphine. Typical reaction conditions include use of a pressure in the range of from about 4 bar to about 75 bar, a temperature in the range of from about 75° C. to about 120° C., and a carbon monoxide partial pressure of from about 0.2 bar to about 2.5 bar.

The hydroformylation process of the invention is also applicable to hydroformylation of olefinic compounds containing one or more internal olefin groups of the formula $>C:C<$, which may be substituted by one or more non-interfering substituents, such as ether groups or ester groups. Typical olefinic compounds containing internal olefin groups include cis- and trans-2-butene, cis- and trans-2- and 3-hexene, cis- and trans-2, -3-, and 4-heptene, cis- and trans-2-, -3-, and -4-octene, cis- and trans-4-nonene, cis- and trans-4-decene, 2-methyl-2-heptene, 2-methyl-2-pentene, cis- and trans-3-methyl-2-pentene, diethyl maleate, and the like.

When hydroformylating compounds containing one or more internal olefinic groups, such as trans-2-heptene, the ligand is preferably a triarylphosphite, such as triphenylphosphite, or a cyclic phosphite, such as one of the cyclic phosphites recommended in EP-A-No. 096988. Further teachings regarding the use of triphenylphosphite in a continuous process for hydroformylation of internal olefinic compounds can be obtained from EP-A-No. 096987.

The use of cyclic phosphites as ligands in the continuous hydroformylation of alpha-olefinic compounds is described in EP-A-No. 0096986.

The liquid hydroformylation medium contains a rhodium complex hydroformylation catalyst comprising rhodium in complex combination with carbon monoxide and with the ligand. Such catalysts can be preformed and introduced into the reaction medium; alternatively the active catalyst species can be prepared in situ from suitable catalyst precursor, such as (2,4-pentane dionato) dicarbonyl rhodium (I). Such methods for preparing the active catalyst species are well known in the art.

The rhodium concentration in the reaction medium preferably ranges from about 20 ppm to about 500 ppm or more, calculated as rhodium metal. However, in view of the expense of rhodium, the preferred rhodium concentration is from about 120 ppm up to about 300 ppm, calculated as rhodium metal.

The reaction medium contains free ligand, that is to say ligand that is not in the form of a rhodium complex. Usually the ligand:rhodium molar ratio in the liquid hydroformylation medium is at least about 2:1, preferably 3:1 or higher up to about 100:1 or more. Preferably there is at least one mole of free ligand per mole of rhodium catalyst. Typically the concentration of ligand in the hydroformylation medium ranges from about 1% by volume up to about 50% by volume, usually from about 5% by volume to about 20% by volume.

The hydroformylation medium contains, in addition to rhodium complex catalyst and free ligand, also product aldehydes, unreacted olefin, minor amounts of by-product hydrogenation product (e.g. the corresponding saturated hydrocarbon when using an alpha-olefin starting material), and aldehyde condensation by-products of the type disclosed in U.S. Pat. No. 4,148,830.

The hydroformylation medium may further include an added inert solvent. Such solvent can be any solvent that acts as a solvent for the catalyst, ligand, starting material, products and by-products and does not react with the aldehyde product or with any other component present in the liquid hydroformylation medium. Alcohols and other materials containing hydroxyl groups, such as alkylene glycols, polyalkylene glycols and mono-ethers and mono-esters thereof, are excluded from consideration since these materials may form high boiling acetals with the aldehyde hydroformylation products and hence contribute to the problems associated with formation of high boiling by-products. As examples of suitable solvents there can be mentioned paraffins and cyclo-paraffins, such as decane, dodecane, tetradecane, octadecane, ($C_1$- to $C_8$-alkyl)decalins, ($C_1$- to $C_8$-alkyl)cyclohexanes, and the like. Other suitable solvents include aromatic compounds, such as ($C_6$- to $C_{12}$-alkyl)-benzenes, ($C_1$- to $C_6$- alkyl)naphthalenes, ($C_1$- to $C_6$-alkyl)-tetralins, o-terphenyl, m-terphenyl, and aryl naphthalenes, such as 1-phenylnaphthalene. Ethers are further examples of suitable inert solvents, such as ($C_1$- to $C_{16}$-alkyl)anisoles (e.g. 1-methoxy-4-ethylbenzene, 1-methoxy-3-n-decylbenzene, and the like), $C_8$ to $C_{18}$ dialkyl ethers (e.g. di-n-butyl ether, di-n-hexyl ether, di-n-octyl ether, di-n-nonyl ether, n-butyl n-decyl ether, and the like), triethylene glycol dimethyl ether, ($C_6$- to $C_{14}$-alkyl)-tetrahydrofurans, ($C_6$- to $C_{14}$-alkyl)-1,4-dioxanes, ($C_1$- to $C_6$-alkyl)-dimethoxybenzenes (e.g. toluhydroquinone dimethyl ether and the like), ($C_6$- to $C_{12}$-alkoxy)-benzenes, and ($C_1$- to $C_{12}$-alkoxy)naphthalenes. Also contemplated for use as the inert solvent are ketones, such as cyclohexanone, ($C_1$- to $C_6$-alkyl) aryl ketones (e.g. acetophenone, propiophenone, n-hexyl phenyl ketone, and the like), ($C_1$- to $C_4$-alkyl) substituted diarylketones, $C_{10}$ to $C_{18}$ dialkylketones, and the like. As further examples of suitable solvents there can be mentioned materials derived from the product aldehydes, including dimethyl acetals, diethyl acetals, 2-alkyl-1,3-dioxolanes, and 2-alkyl-1,3-dioxanes derived from the product aldehyde or aldehydes or from an aldehyde of lower molecular weight than the product aldehyde. Mixtures of two or more solvents can be used.

If such an inert solvent is used in the hydroformylation process of the present invention, then such inert solvent will appear in the vaporous stream from the evaporation zone. When using an added inert solvent, it will usually be preferred to select a solvent that has a boiling point that is at least about 10° C. higher than the boiling point of any product aldehyde at the operating pressure in the fractionation zone so as to facilitate recovery of product aldehydes. In this case the added inert solvent will appear in the liquid bottom stream from the fractionation zone. For further teaching regarding the use of such inert solvents reference should be made to our copending International Patent Application No. PCT/GB 87/00408, filed June 12th 1987.

In order that the invention may be clearly understood and readily carried into effect, a hydroformylation plant designed to operate according to a preferred process in accordance with the invention will now be described, by way of example only, with reference to the accompanying drawing, which is a flow diagram of the plant.

It will be appreciated by those skilled in the art that, as the drawing is diagrammatic, further items of equipment such as temperature and pressure sensors, pressure relief valves, control valves, level controllers and the like would additionally be required in a commercial plant. The provision of such ancillary items of equipment forms no part of the present invention and is in accordance with conventional chemical engineering practice.

Referring to the drawing, a hydroformylation reactor 1 is supplied with purified liquid 1-decene in line 2 at a rate of 47.385 kilograms mols per hour and with a suitably purified synthesis gas mixture containing an approximately 1:1 $H_2$:CO molar mixture in line 3. Reactor 1 is maintained at a total pressure of 8.44 bar, at an $H_2$ partial pressure of 6.21 bar, at a CO partial pressure of 2.07 bar, and at a temperature of 85° C. Reactor 1 contains a charge of a liquid hydroformylation medium containing 250 ppm of rhodium, calculated as rhodium metal, in the form of a rhodium complex hydroformylation catalyst comprising rhodium in complex combination with CO and with triphenylphosphine. The reaction solution also contains excess triphenylphosphine ligand, product $C_{11}$ aldehydes, i.e. a mixture of 1-undecanal and 2-methyldecanal, unreacted 1-decene and "heavies" which comprise aldehyde condensation products of the type disclosed in U.S. Pat. No. 4,148,830. The concentration of triphenylphosphine is 10% w/w, whilst the product $C_{11}$ aldehydes constitute 6.66 mol % of the liquid medium.

Reference numeral 4 indicates a stirrer for reactor 1.

A stream of reaction medium is pumped from reactor 1 in line 5, passes through pressure reduction valve 6, and enters flash vessel 7. This contains a demister pad 8 and is maintained at 1.40 bar. A purge gas stream is taken in line 9, whilst the liquid residue is taken in line 10 to a falling film evaporator, which is heated by steam supplied in line 12. The residence time of reaction medium in falling film evaporator 11 is approximately 2 seconds. Reaction medium exits evaporator 11 at 140° C. and is fed in line 13 to vapour-liquid separator 14 which is fitted with a demister pad 15 and is maintained at 0.03 bar. Substantially all of the $C_{11}$ aldehydes present flash off into the vapour phase and pass on in line 16, together with a minor amount of unreacted 1-decene and any n-decane hydrogenation by-product, to fractionation column 17; this column is operated at 0.02 bar. A catalyst-containing liquid stream collects in the bottom of liquid-vapour separator 14. The liquid level in separator 14 is kept as low as practicable in order to reduce the residence time in separator 14 to a minimum. Typically the residence time of the liquid in separator 14 is about 3 seconds, so that the total residence time in the evaporation zone, from entry to falling film evaporator 11 to exit from separator 14 is no more than about 5 seconds.

From separator 14 the liquid catalyst-containing stream is fed in line 18 to product cooler 19 which is supplied with cooling water in line 20 and serves to cool the liquid stream to 90° C. The cooled catalyst-containing stream is recycled to hydroformylation reactor 1 by way of lines 20 and 21 by means of catalyst recycle pump 22.

Fractionation column 17 contains packing 23. A vaporous product stream containing product $C_{11}$ aldehydes is recovered overhead in line 24 and is condensed in condenser 25 which is supplied with cooling water in line 26. Aldehyde condensate is collected in condensate drum 27 which is connected to a vacuum pump (not shown) by line 28. This vacuum pump maintains the desired low pressure in vapour-liquid separator 14 and in fractionation column 17.

Liquid aldehyde product is recovered in line 29 by means of pump 30. A reflux stream is returned to the top of fractionation column 17 in line 31, the remainder of the product aldehyde passing on to storage in line 32.

A liquid bottom stream is recovered from the bottom of fractionation column 17 in line 33 with the aid of pump 34. Part of this stream is recycled to fractionation column 17 in line 35 via column reboiler 36 which is supplied with steam in line 37. (If desired the lower part of column 17 can be replaced by a falling film evaporator or by a wiped film evaporator). The remainder of the bottom stream from fractionation column 17 is taken in line 38, a part being passed to storage in line 39 for subsequent recovery of triphenylphosphine ligand and "heavies", including aldehyde condensation products, whilst the remainder is recycled to hydroformylation reactor 1 in line 40. The rate of removal of liquid bottom stream in line 39 corresponds to the rate of formation of aldehyde condensation by-products in reactor 1.

The approximate compositions of the various streams in kilogram mols per hour is given in the following Table, which also indicates the pressure and temperature thereof.

TABLE

| COMPONENT (Kg Mol/Hr) | LINE NO. 5 | 9 | 10 | 16 | 18 | 40 | 32 | 28 |
|---|---|---|---|---|---|---|---|---|
| $H_2$ | 0.0663 | 0.0622 | 0.0041 | Trace | — | — | — | Trace |
| $H_2O$ | 0.0065 | Trace | 0.0064 | Trace | — | — | — | Trace |
| CO | 0.091 | 0.0828 | 0.008 | Trace | — | — | — | Trace |
| $CO_2$ | 0.1405 | 0.0972 | 0.0433 | 0.043 | — | — | — | 0.043 |
| $CH_4$ | 0.4154 | 0.3487 | 0.1027 | Trace | — | — | — | Trace |
| Triphenylphosphine | 3.2991 | — | 3.2991 | 0.1207 | 3.1784 | 0.1207 | — | — |
| 1-decene | 2.7891 | 0.0021 | 2.7870 | 2.7331 | Trace | — | 3.463 | 0.027 |
| 1-decane | 0.7731 | Trace | 0.7730 | 0.7569 | Trace | — | | |
| 2-methyl-1-decanal | 3.2814 | | 3.2811 | 2.9474 | 0.3337 | 0.001 | 2.9439 | 0.0167 |
| 1-undecanal | 35.5588 | 0.002 | 35.5567 | 30.877 | 4.6797 | 0.0273 | 30.8355 | |
| "HEAVIES" | 3.1139 | — | 3.1139 | Trace | 3.0910 | 0.0229 | — | — |
| TOTAL | 49.535 | 0.595 | 48.975 | 37.593 | 11.345 | 0.172 | 37.264 | 0.164 |
| PRESSURE (BAR) | 10.345 | 1.40 | 1.40 | 0.028 | 0.028 | 0.0281 | 0.02 | 0.020 |
| TEMP (°C.) | 90.0 | 90 | 90.0 | 140.0 | 140.0 | 168.8 | 68.5 | 68.5 |

What is claimed is:

1. A process for the recovery of a $C_7$ to $C_{17}$ aldehyde, optionally substituted with one or more ether or ester groups, from an organic liquid hydroformylation product medium obtained by rhodium catalysed homogeneous liquid phase hydroformylation of a $C_6$ to $C_{16}$ olefin optionally substituted with one or more ether or ester groups which liquid medium contains (i) a rhodium complex hydroformylation catalyst containing rhodium in complex combination with carbon monoxide and with a ligand, (ii) excess ligand, (iii) at least one $C_7$ to $C_{17}$ aldehyde optionally substituted with one or more ether or ester group and (iv) aldehyde condensation products in addition to dissolved carbon monoxide and hydrogen, which process comprises:
   (a) degassing said liquid hydroformylation medium to produce a degassed liquid hydroformylation medium that is substantially free from dissolved carbon monoxide;
   (b) passing the degassed liquid hydroformylation medium through an evaporation zone maintained under temperature and pressure conditions conducive to evaporation of said at least one $C_7$ to $C_{17}$ aldehyde thereby to effect evaporation of said at least one $C_7$ to $C_{17}$ aldehyde substantially in the absence of carbon monoxide;
   (c) recovering from the evaporation zone a liquid catalyst-containing stream;
   (d) cooling the catalyst-containing stream exiting the evaporation zone;
   (e) recovering a vaporous stream from the vaporation zone containing (i) at least one $C_7$ to $C_{17}$ aldehyde optionally substituted with one or more ether or ester groups, (ii) ligand and (iii) a minor amount of said aldehyde condensation products;
   (f) passing said vaporous stream to a fractionation zone thereby to effect fractionation of the vaporous stream substantially in the absence of carbon monoxide;
   (g) recovering from said fractionation zone (i) a vaporous product stream containing said at least one $C_7$ to $C_{17}$ aldehyde, and (ii) a liquid bottom stream containing said ligand and aldehyde condensation products; and
   (h) recycling said cooled catalyst-containing stream of step (d) and at least a part of the material of said ligand bottom stream of step (g) to said hydroformylation zone.

2. A process according to claim 1, in which the evaporation zone is operated at a temperature in the range of from about 100° C. to about 170° C. and at a pressure in the range of from about 0.0001 bar up to about 0.05 bar.

3. A process according to claim 1, in which the residence time in the evaporation zone is from about 0.5 to about 5 seconds.

4. A process according to claim 1, in which the hydroformylation medium contains said catalyst and said free ligand dissolved in a "natural process solvent" comprising unreacted olefin, aldehyde products, and aldehyde condensation products.

5. A process according to claim 1, in which the hydroformylation medium contains an added inert solvent.

6. A process according to claim 5, in which the added inert solvent is less volatile than any optionally substituted $C_7$ to $C_{17}$ aldehyde formed in the hydroformylation reaction but is more volatile than the ligand.

7. A process according to claim 1, in which the evaporation zone comprises a falling film or wiped film evaporator.

8. A process for the production of a $C_7$ to $C_{17}$ aldehyde optionally substituted with one or more ether or ester groups by rhodium catalysed hydroformylation of a $C_6$ to $C_{16}$ olefin optionally substituted with one or more ester groups which comprises feeding said olefin and make-up quantitites of carbon monoxide and hydrogen to a hydroformylation zone containing a predetermined volume of a liquid hydroformylation medium containing a rhodium complex hydroformylation catalyst comprising rhodium in complex combination with carbon monoxide and with a ligand, and excess ligand; withdrawing liquid hydroformylation medium from the hydroformylation zone; degassing this withdrawn hydroformylation medium; passing degassed liquid hydroformylation medium through an evaporation zone maintained under temperature and pressure conditions conducive to evaporation of said at least one $C_7$ to $C_{17}$ aldehyde optionally substituted with one or more ether or ester groups; recovering from the evaporation zone a liquid catalyst-containing stream; cooling said catalyst-containing stream exiting the evaporation zone; recycling cooled catalyst-containing stream to the hydroformylation zone; recovering a vaporous stream from the evaporation zone containing said at least one $C_7$ to $C_{17}$ aldehyde optionally substituted with one or more ether or ester groups, ligand and a minor amount of aldehyde condensation products; passing said vaporous stream to a fractionation zone; recovering from said fractionation zone a vaporous product stream containing said at least one $C_7$ to $C_{17}$ aldehyde optionally substituted with one or more ether or ester groups and a liquid bottom stream containing ligand and aldehyde condensation products; and recycling sufficient of the material of said liquid bottom stream to said hydroformylation zone to maintain said predetermined volume of hydroformylation medium therein.

9. A process according to claim 8, in which the evaporation zone is operated at a temperature in the range of from about 100° C. to about 170° C. and at a pressure in the range of from about 0.001 bar up to about 0.05 bar.

10. A process according to claim 8, in which the residence time in the evaporation zone is from about 0.5 to about 5 seconds.

11. A process according to claim 8, in which the hydroformylation medium contains said catalyst and said free ligand dissolved in a "natural process solvent" comprising unreacted olefin, aldehyde products, and aldehyde condensation products.

12. A process according to claim 8, in which the hydroformylation medium contains an added inert solvent.

13. A process according to claim 12, in which the added inert solvent is less volatile than any optionally substituted $C_7$ to $C_{17}$ aldehyde formed in the hydroformylation reaction but is more volatile than the ligand.

14. A process according to claim 8, in which the evaporation zone comprises a falling film or wiped film evaporator.

* * * * *